US008580951B2

(12) United States Patent
Lu et al.

(10) Patent No.: US 8,580,951 B2
(45) Date of Patent: *Nov. 12, 2013

(54) ALDEHYDE-FUNCTIONALIZED POLYSACCHARIDES

(75) Inventors: Helen S. M. Lu, Wallingford, PA (US); Steven W. Shuey, Chadds Ford, PA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 269 days.

This patent is subject to a terminal disclaimer.

(21) Appl. No.: 12/996,477

(22) PCT Filed: Jul. 1, 2010

(86) PCT No.: PCT/US2010/040702
§ 371 (c)(1),
(2), (4) Date: Dec. 6, 2010

(87) PCT Pub. No.: WO2011/002956
PCT Pub. Date: Jan. 6, 2011

(65) Prior Publication Data
US 2012/0004194 A1    Jan. 5, 2012

Related U.S. Application Data

(60) Provisional application No. 61/222,725, filed on Jul. 2, 2009.

(51) Int. Cl.
| C08B 1/00 | (2006.01) |
| C08B 11/02 | (2006.01) |
| C08B 11/04 | (2006.01) |
| C08B 11/08 | (2006.01) |
| C08B 11/12 | (2006.01) |
| C08B 31/18 | (2006.01) |
| C08B 37/02 | (2006.01) |
| C08B 37/12 | (2006.01) |
| C08B 37/18 | (2006.01) |
| C08L 1/02 | (2006.01) |
| C08L 1/28 | (2006.01) |
| C08L 5/02 | (2006.01) |
| C08L 5/08 | (2006.01) |
| C08L 5/12 | (2006.01) |

(52) U.S. Cl.
USPC ........... 536/112; 536/55.1; 536/55.2; 536/56; 536/84; 536/96; 536/97; 536/98; 536/104; 536/105; 536/123.12; 514/54; 514/57; 514/59; 514/60

(58) Field of Classification Search
None
See application file for complete search history.

(56) References Cited

U.S. PATENT DOCUMENTS

| 4,584,188 A | 4/1986 | Graham |
| 4,703,116 A | 10/1987 | Solarek et al. |
| 4,731,162 A | 3/1988 | Solarek et al. |
| 4,741,804 A | 5/1988 | Solarek et al. |
| 4,749,800 A | 6/1988 | Jobe et al. |
| 4,766,245 A | 8/1988 | Larkin et al. |
| 5,092,883 A | 3/1992 | Eppley et al. |
| 5,116,824 A | 5/1992 | Miyata et al. |
| 5,162,430 A | 11/1992 | Rhee et al. |
| 5,196,441 A | 3/1993 | Kunisch et al. |
| 5,275,838 A | 1/1994 | Merrill |
| 5,292,802 A | 3/1994 | Rhee et al. |
| 5,308,889 A | 5/1994 | Rhee et al. |
| 5,324,775 A | 6/1994 | Rhee et al. |
| 5,328,955 A | 7/1994 | Schaulin et al. |
| 5,451,398 A | 9/1995 | Vigh |
| 5,502,042 A | 3/1996 | Gruskin et al. |
| 5,505,952 A | 4/1996 | Jiang et al. |
| 5,514,379 A | 5/1996 | Weissleder et al. |
| 5,567,685 A | 10/1996 | Linden et al. |
| 5,643,575 A | 7/1997 | Martinez et al. |
| 5,733,563 A | 3/1998 | Fortier |
| 5,830,986 A | 11/1998 | Merrill et al. |
| 5,840,698 A | 11/1998 | Campbell et al. |
| 5,843,865 A | 12/1998 | Del Corral et al. |
| 5,874,500 A | 2/1999 | Rhee et al. |
| 6,051,648 A | 4/2000 | Rhee et al. |
| 6,121,375 A | 9/2000 | Eknoian |
| 6,150,472 A | 11/2000 | Engbers |
| 6,165,488 A | 12/2000 | Tardy et al. |
| 6,166,130 A | 12/2000 | Rhee et al. |

(Continued)

FOREIGN PATENT DOCUMENTS

| JP | 1982-102932 | 6/1982 |
| JP | 1988-11167 | 1/1988 |

(Continued)

OTHER PUBLICATIONS

Ahmad, S., et al Dextran and 5-aminosalicylic acid (5-ASA) conjugates . . . Carbohyd. Res. (2006) vol. 341, pp. 2694-2701.*

(Continued)

Primary Examiner — Leigh Maier
(74) Attorney, Agent, or Firm — McCarter & English

(57) ABSTRACT

Novel aldehyde-functionalized polysaccharide compositions are described that are more stable in aqueous solution than oxidized polysaccharides or other types of polysaccharides containing pendant aldehyde groups. The aldehyde-functionalized polysaccharides may be reacted with various amine-containing polymers to form hydrogel tissue adhesives and sealants that may be useful for medical applications such as wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, drug delivery, and preventing post-surgical adhesions.

8 Claims, No Drawings

(56) References Cited

U.S. PATENT DOCUMENTS

| | | | |
|---|---|---|---|
| 6,323,278 B2 | 11/2001 | Rhee et al. | |
| 6,391,939 B2 | 5/2002 | Tayot et al. | |
| 6,410,519 B1 | 6/2002 | Gruskin et al. | |
| 6,458,147 B1 | 10/2002 | Cruise et al. | |
| 6,458,889 B1 | 10/2002 | Trollsas et al. | |
| 6,465,694 B1 | 10/2002 | Baudys et al. | |
| 6,514,534 B1 | 2/2003 | Sawhney | |
| 6,534,591 B2 | 3/2003 | Rhee et al. | |
| 6,602,952 B1 | 8/2003 | Bentley et al. | |
| 6,620,125 B1 | 9/2003 | Redl | |
| 6,696,089 B2 | 2/2004 | Kalbanov et al. | |
| 6,703,047 B2 | 3/2004 | Sawhney et al. | |
| 6,756,518 B2 | 6/2004 | Gruskin et al. | |
| 6,800,278 B1 | 10/2004 | Perrault et al. | |
| 6,833,408 B2 | 12/2004 | Sehl et al. | |
| 6,858,736 B2 | 2/2005 | Nho et al. | |
| 6,896,725 B2 | 5/2005 | Thornton et al. | |
| 7,217,845 B2 | 5/2007 | Rosen et al. | |
| 7,834,065 B2 | 11/2010 | Nakajima et al. | |
| 7,960,498 B2 | 6/2011 | Chenault et al. | |
| 2002/0151520 A1 | 10/2002 | Gruskin | |
| 2003/0022216 A1 | 1/2003 | Mao et al. | |
| 2003/0027788 A1 | 2/2003 | Singh et al. | |
| 2003/0064502 A1 | 4/2003 | Illman et al. | |
| 2003/0087111 A1 | 5/2003 | Hubbell et al. | |
| 2003/0108511 A1 | 6/2003 | Sawhney | |
| 2003/0119985 A1 | 6/2003 | Sehl et al. | |
| 2004/0072793 A1* | 4/2004 | Aeschlimann et al. | 514/54 |
| 2004/0086479 A1 | 5/2004 | Grinstaff et al. | |
| 2004/0096507 A1 | 5/2004 | Kwant et al. | |
| 2004/0225097 A1 | 11/2004 | Nho et al. | |
| 2004/0235708 A1 | 11/2004 | Rhee et al. | |
| 2005/0002893 A1 | 1/2005 | Goldmann | |
| 2005/0020805 A1 | 1/2005 | Sunkara et al. | |
| 2005/0288684 A1 | 12/2005 | Aronson et al. | |
| 2006/0078536 A1 | 4/2006 | Kodokian et al. | |
| 2006/0115531 A1 | 6/2006 | Chenault | |
| 2006/0193899 A1 | 8/2006 | Sawhney | |
| 2006/0292030 A1 | 12/2006 | Odermatt et al. | |
| 2007/0031467 A1 | 2/2007 | Abrahams et al. | |
| 2007/0048251 A1 | 3/2007 | Arthur | |
| 2007/0249870 A1 | 10/2007 | Chenault | |
| 2008/0220047 A1 | 9/2008 | Sawhney et al. | |
| 2008/0319101 A1 | 12/2008 | Nakajima et al. | |
| 2009/0035249 A1 | 2/2009 | Bhatia et al. | |
| 2009/0054535 A1 | 2/2009 | Figuly et al. | |
| 2010/0086678 A1 | 4/2010 | Arthur et al. | |
| 2010/0112063 A1 | 5/2010 | Figuly et al. | |
| 2010/0272804 A1 | 10/2010 | Lu | |
| 2011/0224724 A1 | 9/2011 | Lu et al. | |
| 2011/0250257 A1 | 10/2011 | Arthur et al. | |
| 2011/0269916 A1 | 11/2011 | Chenault et al. | |

FOREIGN PATENT DOCUMENTS

| | | |
|---|---|---|
| WO | WO 87/00836 | 2/1987 |
| WO | WO 90/10441 | 9/1990 |
| WO | WO 91/15368 | 10/1991 |
| WO | WO 97/30103 | 8/1997 |
| WO | WO 99/01143 | 1/1999 |
| WO | 99/07744 A1 | 2/1999 |
| WO | WO 00/69925 | 11/2000 |
| WO | WO 01/49268 | 7/2001 |
| WO | WO 01/72280 | 10/2001 |
| WO | 01/87986 A1 | 11/2001 |
| WO | WO 02/102864 | 12/2002 |
| WO | WO 03/020818 | 3/2003 |
| WO | WO 03/097759 | 11/2003 |
| WO | WO 2006/031358 | 3/2006 |
| WO | WO 2006/042161 | 4/2006 |
| WO | WO 2006/080523 | 8/2006 |
| WO | WO 2006/086510 | 8/2006 |
| WO | WO 2008/005207 | 1/2008 |
| WO | WO 2008/066787 | 6/2008 |
| WO | WO 2009/064977 | 5/2009 |
| WO | 2010/111570 A1 | 9/2010 |

OTHER PUBLICATIONS

Thome, J., et al., "Ultrathin Antibacterial Polyammonium Coatings on Polymer Surfaces"; Surface and Coatings Technology, 174-175, 2003, pp. 584-587.

Harris, J. Milton, "Laboratory Synthesis of Polyethylene Glycol Derivatives", JMS—Rev., Macromol. Chem. Phys., C25 (3), 1985, pp. 325-373.

Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.

Chen, Nicole, et al., "Mechanisms of Aldehyde-Containing Paper Wet-Strength Resins", Industrial & Engineering Chemistry Research, vol. 41, No. 22, 2002, pp. 5366-5371.

Callant, Dominique, et al., "A New Approach to Dextran Derivatives with Pendent Aldehyde Groups", Reactive Polymers, vol. 8, 1988, pp. 129-136.

Hollander, Andreas, et al., "Polymer Surface Chemistry for Biologically Active Materials", Applied Surface Science, vol. 235, 2004, pp. 145-150.

Stone, H. Harlan, et al., "Antibiotic Prophylaxis in Gastric, Biliary and Colonic Surgery", Ann. Surg; Oct. 1976, pp. 443-450.

Fishman, Alexander, et al., "Synthesis and Investigation of Novel Branched PEG-Based Soluble Polymer Supports", The Journal of Organic Chemistry, vol. 68, 2003, pp. 9843-9846.

Newkome, George R., "Improved Synthesis of an Ethereal Tetraamine Core for Dendrimer Construction", The Journal of Organic Chemistry, vol. 67, 2002, pp. 3957-3960.

Halabi, A., et al., "Synthesis and Characterization of a Novel Dendritic Acrylic Monomer", The Journal of Organic Chemistry, vol. 65, 2000, pp. 9210-9213.

Harris, J. Milton, et al., "Synthesis and Characterization of Poly(ethylene Glycol) Derivatives", Journal of Polymer Science: Polymer Chemistry Edition, vol. 22, 1984, pp. 341-352.

Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.

Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.

Azzam, Tony, et al., "Cationic Polysaccharides for Gene Delivery", Macromolecules, vol. 35, No. 27, 2002, pp. 9947-9953.

Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.

Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.

Zalipsky, Samuel, et al., "Preparation and Applications of Polyethylene Glycol-Polystyrene Graft Resin Supports for Solid-Phase Peptide Synthesis", Reactive Polymers, vol. 22, 1994, pp. 243-258.

Lara, V.S., et al., "Dentin-Induced In Vivo Inflammatory Response and In Vitro Activation of Murine Macrophages", Journal of Dental Research, vol. 82, No. 6, 2003, pp. 460-465.

Atassi, M.Z., "Immunochemistry of Proteins", vol. 1, Plenum Press, New York, 1977, pp. 59-60.

Sweeney, Thomas, et al., "Intestinal Anastomoses Detected with a Photopolymerized Hydrogel", Surgery, vol. 131, No. 2, Feb. 2002, pp. 185-189.

(56) References Cited

OTHER PUBLICATIONS

Kim, Jae Chan, et al., "Evaluation of Tissue Adhesives in Closure of Scleral Tunnel Incisions", Journal of Cataract & Refractive Surgery, vol. 21, May 1995, pp. 320-325.

Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.

Buckmann, Andreas F., et al., "Functionalization of Poly(ethylene glycol) and Monomethoxy-Poly(ethylene glycol)", Makromolecular Chemistry, vol. 182, 1981, pp. 1379-1384.

Bruce, J., et al., "Systematic Review of the Definition and Measurement of Anastomotic Leak after Gastrointestinal Surgery", British Journal of Surgery, vol. 88, 2001, pp. 1157-1168.

Mo, Xiumei, et al,, "Soft Tissue Adhesive Composed of Modified Gelatin and Polysaccharides", Journal of Biomaterials Science Polymer Edition, vol. 11, No. 4, 2000, pp. 341-351.

Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.

Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.

Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.

Pfannemuller, B., et al., "Chemical Modification of the Surface of the Starch Granules", Starch/Starke, vol. 95, No. 9, 1983, pp. 298-303.

International Search Report, PCT/US2010/040702, Dated: Sep. 29, 2010.

\* cited by examiner

ALDEHYDE-FUNCTIONALIZED POLYSACCHARIDES

CROSS-REFERENCE TO RELATED APPLICATIONS

This application claims priority under 35 U.S.C. §119 from U.S. Provisional Application Ser. No. 61/222,725 filed on Jul. 2, 2009.

FIELD OF THE INVENTION

The invention relates to the field of medical adhesives and sealants. More specifically, the invention relates to novel aldehyde-functionalized polysaccharides containing pendant aldehyde groups that are useful for forming hydrogel tissue adhesives and sealants for medical use.

BACKGROUND OF THE INVENTION

Tissue adhesives and sealants have many potential medical applications, including wound closure, supplementing or replacing sutures or staples in internal surgical procedures, preventing leakage of fluids such as blood, bile, gastrointestinal fluid and cerebrospinal fluid, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, fibrin-based adhesives do not bond covalently to the underlying tissue.

Several types of hydrogel tissue adhesives have been developed, which have improved adhesive and cohesive properties and are nontoxic. These hydrogels are generally formed by reacting a component having nucleophilic groups with a component having electrophilic groups that are capable of reacting with the nucleophilic groups of the first component, to form a crosslinked network via covalent bonding. A number of these hydrogel tissue adhesives are prepared using an oxidized polysaccharide containing aldehyde groups as one of the reactive components (see for example, Kodokian et al., copending and commonly owned U.S. Patent Application Publication No. 2006/0078536, Goldmann, U.S. Patent Application Publication No. 2005/0002893, and Nakajima et al., U.S. Patent Application Publication No. 2008/0319101). However, the instability of oxidized polysaccharides in aqueous solution limits their shelf-life for commercial use.

Callant et al. (*Reactive Polymers, Ion Exchangers, Sorbents* 8(2):129-136, 1988) describe soluble dextran derivatives containing aldehyde side groups that are prepared by reacting a 4-nitrophenyl carbonate ester of dextran with 2,3-dihydroxypropylamine and subsequent selective periodate oxidation of the pendant diol groups. However, the resulting dextran aldehydes were unstable when heated in mildly acidic media, undergoing aldol reactions.

Therefore, the need exists for polysaccharides containing aldehyde groups, which are more stable in aqueous solution than oxidized polysaccharides, for use in forming hydrogel tissue adhesives and sealants for medical use.

SUMMARY OF THE INVENTION

The present invention addresses the above need by providing aldehyde-functionalized polysaccharides containing pendant aldehyde groups that are more stable in aqueous solution than oxidized polysaccharides and may be reacted with various amine-containing polymers to form hydrogel tissue adhesives and sealants, which have desirable properties for medical applications.

Accordingly, in one embodiment the invention provides a composition comprising at least one aldehyde-functionalized polysaccharide containing pendant aldehyde groups, said aldehyde-functionalized polysaccharide having a weight-average molecular weight of about 1,000 to about 1,000,000 Daltons and a degree of aldehyde substitution of greater than 30% to about 200%;
wherein:
(i) said pendant aldehyde groups are attached to the polysaccharide through linking groups which do not contain a nitrogen atom; and
(ii) said linking groups are attached to the polysaccharide by ether linkages.

DETAILED DESCRIPTION

As used above and throughout the description of the invention, the following terms, unless otherwise indicated, shall be defined as follows:

The term "pendant aldehyde group" refers to an aldehyde group that is attached to the carbohydrate of the polysaccharide via one of the ring hydroxyl groups. The pendant aldehyde groups may be single aldehyde groups or dialdehydes.

The term "ether linkage" refers to a chemical linkage of two substituted or unsubstituted alkyl or aryl groups through an oxygen atom, (i.e., R—O—R').

The term "degree of aldehyde substitution" refers to the mole percent of pendant aldehyde groups per mole of carbohydrate repeat units, i.e., (moles of pendant aldehyde groups/moles of carbohydrate repeat units)×100.

The term "water-dispersible, multi-arm polyether amine" refers to a polyether having three or more polymer chains ("arms"), which may be linear or branched, emanating from a central structure, which may be a single atom, a core molecule, or a polymer backbone, wherein at least three of the branches ("arms") are terminated by a primary amine group. The water-dispersible, multi-arm polyether amine is water soluble or is able to be dispersed in water to form a colloidal suspension capable of reacting with a second reactant in aqueous solution or dispersion.

The term "dispersion" as used herein, refers to a colloidal suspension capable of reacting with a second reactant in an aqueous medium.

The term "polyether" refers to a polymer having the repeat unit [—O—R]—, wherein R is a hydrocarbylene group having 2 to 5 carbon atoms. The polyether may also be a random or block copolymer comprising different repeat units which contain different R groups.

The term "hydrocarbylene group" refers to a divalent group formed by removing two hydrogen atoms, one from each of two different carbon atoms, from a hydrocarbon.

The term "primary amine" refers to a neutral amino group having two free hydrogens. The amino group may be bound to a primary, secondary or tertiary carbon.

The term "crosslink" refers to a bond or chain of atoms attached between and linking two different polymer chains.

The term "% by weight", also referred to herein as "wt %" refers to the weight percent relative to the total weight of the solution or dispersion, unless otherwise specified.

The term "anatomical site" refers to any external or internal part of the body of humans or animals.

The term "tissue" refers to any biological tissue, both living and dead, in humans or animals.

The term "hydrogel" refers to a water-swellable polymeric matrix, consisting of a three-dimensional network of macromolecules held together by covalent crosslinks that can absorb a substantial amount of water to form an elastic gel.

The term "PEG" as used herein refers to poly(ethylene glycol).

The term "$M_w$" as used herein refers to the weight-average molecular weight.

The term "$M_n$" as used herein refers to the number-average molecular weight.

The term "$M_z$" as used herein refers to the z-average molecular weight.

The term "medical application" refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "mol %" means mole percent, "Vol" means volume, "w/w" means weight per weight, "Da" means Daltons, "kDa" means kiloDaltons, the designation "10K" means that a polymer molecule possesses a number-average molecular weight of 10 kiloDaltons, "M" means molarity, "kPa" means kilopascals, "psi" means pounds per square inch, "rpm" means revolutions per minute", "$^1$H NMR" means proton nuclear magnetic resonance spectroscopy, "13-C NMR" means carbon 13 nuclear magnetic resonance spectroscopy, "ppm" means parts per million, "cP" means centipoise, PBS" means phosphate-buffered saline, "MWCO" means molecular weight cut off.

A reference to "Aldrich" or a reference to "Sigma" means the said chemical or ingredient was obtained from Sigma-Aldrich, St. Louis, Mo.

Disclosed herein are aldehyde-functionalized polysaccharides containing pendant aldehyde groups. The aldehyde-functionalized polysaccharides may be reacted with various amine-containing polymers to form hydrogel tissue adhesives and sealants, which have desirable properties for medical applications. The aldehyde-functionalized polysaccharides are more stable in aqueous solution than are oxidized polysaccharides, thereby, making their use more practical for commercial purposes. The hydrogel tissue adhesives and sealants prepared using the aldehyde-functionalized polysaccharides may be useful for medical and veterinary applications, including, but not limited to, wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, drug delivery, and preventing post-surgical adhesions.

Aldehyde-Functionalized Polysaccharides

The aldehyde-functionalized polysaccharides disclosed herein are polysaccharides that have been chemically modified to introduce pendant aldehyde groups into the molecule. The pendant aldehyde groups may be single aldehyde groups or dialdehydes. The pendant aldehyde groups of the aldehyde-functionalized polysaccharides disclosed herein are attached to the polysaccharide through linking groups. The linking groups comprise carbon, hydrogen, and oxygen atoms, but do not contain a nitrogen atom, and are attached to the polysaccharide by ether linkages. As demonstrated in the Examples herein below, aldehyde-functionalized polysaccharides having these types of linking groups are more stable in aqueous solution that oxidized polysaccharides or aldehyde-functionalized polysaccharides having other types of linking groups, such as those that contain a nitrogen atom or are linked to the polysaccharide by other chemical linkages (e.g., amide or urethane). In one embodiment, the linking group contains an alkoxy group alpha to the pendant aldehyde group (i.e., on an adjacent carbon atom). In another embodiment, the linking group does not contain an alkoxy group beta to the pendant aldehyde group (i.e., on the second carbon atom from the aldehyde group).

As used herein, aldehyde-functionalized polysaccharides do not include polysaccharides that are oxidized by cleavage of the polysaccharide rings to introduce aldehyde groups. Oxidation of the polysaccharide rings results in dialdehydes formed by opening the rings of the polysaccharide. Therefore, the dialdehyde groups formed by oxidation of polysaccharide rings are not pendant aldehyde groups as defined herein.

Aldehyde-functionalized polysaccharides may be prepared by chemically modifying a polysaccharide to introduce pendant aldehyde groups. Useful aldehyde-functionalized polysaccharides include, but are not limited to, aldehyde-functionalized derivatives of: dextran, carboxymethyldextran, starch, agar, cellulose, hydroxyethylcellulose, carboxymethylcellulose, pullulan, inulin, levan, and hyaluronic acid. The starting polysaccharides are available commercially from sources such as Sigma Chemical Co. (St. Louis, Mo.). Typically, polysaccharides are a heterogeneous mixture having a distribution of different molecular weights, and are characterized by an average molecular weight, for example, the weight-average molecular weight ($M_w$), or the number average molecular weight ($M_n$), as is known in the art. Therefore, the aldehyde-functionalized polysaccharides prepared from these polysaccharides are also a heterogeneous mixture having a distribution of different molecular weights. Suitable aldehyde-functionalized polysaccharides have a weight-average molecular weight of about 1,000 to about 1,000,000 Daltons, more particularly about 3,000 to about 250,000 Daltons, more particularly about 5,000 to about 60,000 Daltons, and more particularly about 7,000 to about 20,000 Daltons. In one embodiment, the aldehyde-functionalized polysaccharide is aldehyde-functionalized dextran. In another embodiment, the aldehyde-functionalized polysaccharide is aldehyde-functionalized inulin.

Aldehyde-functionalized polysaccharides may be prepared using methods known in the art. Aldehyde-functionalized polysaccharides may be prepared using any of the methods described by Mehta et al. (WO 99/07744). For example, dextran may be reacted with allyl glycidyl ether in an acid aqueous medium to form allyloxy dextran which is then oxidized by ozonolysis to cleave the double bond and introduce a terminal aldehyde group, as described in detail in the Examples herein below. Additionally, glycidol may be reacted with a polysaccharide, such as dextran, in a basic aqueous medium to give an alkylated polysaccharide, as described by Chen (*Biotechnology Techniques* 3:131-134, 1989). Periodate oxidation of the alkylated polysaccharide yields an aldehyde-functionalized polysaccharide having pendant aldehyde groups. The aldehyde-functionalized polysaccharides may also be prepared by the method described by Solarek et al. (U.S. Pat. No. 4,703,116) wherein a polysaccharide is reacted with a derivatizing acetal reagent in the presence of base and then the acetal is hydrolyzed by adjusting the pH to less than 7.0.

Aldehyde-functionalized polysaccharides having dialdehyde functional groups can be prepared by first attaching a pendant group containing either a terminal diene or by attaching a cyclic, disubstituted olefin to the polysaccharide ring. Attachment of the pendant groups can be accomplished using a variety of methods, including reaction of the polysaccharide with glycidyl ethers containing cyclic olefins or terminal dienes, or reaction with carboxylic acids or derivatives thereof which also contain cyclic olefins or terminal dienes. Oxidation of the polysaccharides derivatized with cyclic olefins or terminal dienes using methods known in the art, such as ozonolysis, yield polysaccharides derivatized with pendant dialdehydes.

The degree of aldehyde substitution may be determined using methods known in the art. For example, the degree of aldehyde substitution may be determined by titrating the aldehyde-functionalized polysaccharide with hydroxyl amine hydrochloride according to the method of Zhao and Heindel (*Pharmaceutical Research* 8:400, 1991). Suitable aldehyde-functionalized polysaccharides have a degree of aldehyde substitution of greater than 30% to about 200%, more particularly greater than 33% to about 200%, more particularly 35% to about 200%, and more particularly about 40% to about 120%.

Hydrogel Tissue Adhesives and Sealants

The aldehyde-functionalized polysaccharides described above may be used in combination with various amine-containing polymers to prepare hydrogel tissue adhesives and sealants for medical and veterinary applications, including, but not limited to, wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, drug delivery, and preventing post-surgical adhesions. For example, an aldehyde-funtionalized polysaccharide may be used in place of an oxidized polysaccharide to react with a multi-arm polyether amine (Kodokian et al., copending and commonly owned U.S. Patent Application Publication No. 2006/0078536), as described in detail in the Examples herein below. Alternatively, an aldehyde-funtionalized polysaccharide may be used in place of an oxidized polysaccharide to react with a polymer having amino groups such as chitosan or a modified polyvinyl alcohol having amino groups (Goldmann, U.S. Patent Application Publication No. 2005/000289), or with an amino group containing polymer such as poly L-lysine (Nakajima et al., U.S. Patent Application Publication No. 2008/0319101).

The aldehyde-functionalized polysaccharides may be used in various forms to prepare a hydrogel tissue adhesive and sealant. In one embodiment, the aldehyde-functionalized polysaccharide is used in the form of aqueous solution or dispersion. To prepare an aqueous solution or dispersion comprising an aldehyde-functionalized polysaccharide, at least one aldehyde-functionalized polysaccharide is added to water to give a concentration of about 5% to about 40%, more particularly from about 5% to about 30%, more particularly from about 10% to about 30%, and more particularly from about 20% to about 30% by weight relative to the total weight of the solution or dispersion. Additionally, a mixture of at least two different aldehyde-functionalized polysaccharides having different weight-average molecular weights, different degrees of aldehyde substitution (i.e., different equivalent weights per aldehyde group), or both different weight-average molecular weights and degrees of aldehyde substitution may be used. Where a mixture of aldehyde-functionalized polysaccharides is used, the total concentration of the aldehyde-functionalized polysaccharides is about 5% to about 40% by weight, more particularly from about 5% to about 30%, more particularly from about 10% to about 30%, and more particularly from about 20% to about 30% by weight relative to the total weight of the solution or dispersion.

For use as a component to prepare a hydrogel tissue adhesive or sealant, it is preferred that the aqueous solution or dispersion comprising the aldehyde-functionalized polysaccharide be sterilized to prevent infection. Any suitable sterilization method known in the art that does not adversely affect the ability of the aldehyde-functionalized polysaccharide to react to form an effective hydrogel may be used, including, but not limited to, electron beam irradiation, gamma irradiation, ethylene oxide sterilization, or filtration through a 0.2 μm pore membrane.

The aqueous solution or dispersion comprising the aldehyde-functionalized polysaccharide may further comprise various additives depending on the intended application. Preferably, the additive does not interfere with effective gelation to form a hydrogel. The amount of the additive used depends on the particular application and may be readily determined by one skilled in the art using routine experimentation. For example, the aqueous solution or dispersion comprising the aldehyde-functionalized polysaccharide may comprise at least one additive selected from pH modifiers, viscosity modifiers, anti-oxidants, stabilizers, antimicrobials, colorants, surfactants, additives that increase or decrease the rate of degradation of the hydrogel tissue adhesive or sealant, pharmaceutical drugs and therapeutic agents.

The aqueous solution or dispersion comprising the aldehyde-functionalized polysaccharide may optionally include at least one pH modifier to adjust the pH of the solution or dispersion. Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, carboxylates, nitrogen-containing compounds other than primary and secondary amines, and basic carbonates and phosphates.

The aqueous solution or dispersion comprising the aldehyde-functionalized polysaccharide may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate and potassium benzoate; polyhexamethylene biguanide; antibiotics effective against bacteria, including aminoglycoside antibiotics such as gentamicin, streptomycin, amikacin and kanamycin, a cephalosporin such as cephalexin and cephtriaxone, a carbacephem such as loracarbef, a glycopeptide such as vancomycin, a macrolide such as erythromycin and rifampicin, a penicillin such as amoxicillin and ampicillin, a polypeptide such as bacitracin and polymyxin B, a quinolone such as ciprofloxacin, levofloxacin and moxifloxacin, a tetracycline such as oxytetracycline and doxycycline, and a sulfonamide; antifungals such as ketoconazole, miconazole and amphotericin B; antivirals such as acyclovir or AZT; antihelminthics; and antiprotozoals.

The aqueous solution or dispersion comprising the aldehyde-functionalized polysaccharide may optionally include at least one colorant to enhance the visibility of the solution. Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No.

5, D&C Violet No. 2; and natural colorants such as beetroot red, canthaxanthin, chlorophyll, eosin, saffron, and carmine.

The aqueous solution or dispersion comprising the aldehyde-functionalized polysaccharide may optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan. Additionally, the aqueous solution or dispersion comprising the aldehyde-functionalized polysaccharide may optionally include at least one pharmaceutical drug or therapeutic agent. Suitable drugs and therapeutic agents are well known in the art (for example see the United States Pharmacopeia (USP), Physician's Desk Reference (Thomson Publishing), The Merck Manual of Diagnosis and Therapy 18th ed., Mark H. Beers and Robert Berkow (eds.), Merck Publishing Group, 2006; or, in the case of animals, The Merck Veterinary Manual, 9th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anticancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Reagent Preparation

Preparation of Oxidized Dextran (D10-50)

Dextran aldehyde is made by oxidizing dextran in aqueous solution with sodium metaperiodate. An oxidized dextran having an average molecular weight of about 10,000 Da and an oxidation conversion of about 50% (i.e., about half of the glucose rings in the dextran polymer are oxidized to dialdehydes) is prepared from dextran having a weight-average molecular weight of 8,500 to 11,500 Daltons (Sigma) by the method described by Cohen et al. (copending and commonly owned International Patent Application Publication No. WO 2008/133847). A typical procedure is described here.

A 20-L reactor equipped with a mechanical stirrer, addition funnel, internal temperature probe, and nitrogen purge is charged with 1000 g of the dextran and 9.00 L of de-ionized water. The mixture is stirred at ambient temperature to dissolve the dextran and then cooled to 10 to 15° C. To the cooled dextran solution is added over a period of an hour, while keeping the reaction temperature below 25° C., a solution of 1000 g of sodium periodate dissolved in 9.00 L of de-ionized water. Once all the sodium periodate solution has been added, the mixture is stirred at 20 to 25° C. for 4 more hours. The reaction mixture is then cooled to 0° C. and filtered to clarify. Calcium chloride (500 g) is added to the filtrate, and the mixture is stirred at ambient temperature for 30 min and then filtered. Potassium iodide (400 g) is added to the filtrate, and the mixture is stirred at ambient temperature for 30 min. A 3-L portion of the resulting red solution is added to 9.0 L of acetone over a period of 10 to 15 min with vigorous stirring by a mechanical stirrer during the addition. After a few more minutes of stirring, the agglomerated product is separated from the supernatant liquid. The remaining red solution obtained by addition of potassium iodide to the second filtrate is treated in the same manner as above. The combined agglomerated product is broken up into pieces, combined with 2 L of methanol in a large stainless steel blender, and blended until the solid becomes granular. The granular solid is recovered by filtration and dried under vacuum with a nitrogen purge. The granular solid is then hammer milled to a fine powder. A 20-L reactor is charged with 10.8 L of de-ionized water and 7.2 L of methanol, and the mixture is cooled to 0° C. The granular solid formed by the previous step is added to the reactor and the slurry is stirred vigorously for one hour. Stirring is discontinued, and the solid is allowed to settle to the bottom of the reactor. The supernatant liquid is decanted by vacuum, 15 L of methanol is added to the reactor, and the slurry is stirred for 30 to 45 min while cooling to 0° C. The slurry is filtered in portions, and the recovered solids are washed with methanol, combined, and dried under vacuum with a nitrogen purge to give about 600 g of the oxidized dextran, which is referred to herein as D10-50.

The degree of oxidation of the product is determined by proton NMR to be about 50% (equivalent weight per aldehyde group=146). In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH).

Preparation of Eight-Arm PEG 10K Octaamine (P8-10-1):

Eight-arm PEG 10K octaamine (M$_n$=10 kDa) is synthesized using the two-step procedure described by Chenault in co-pending and commonly owned U.S. Patent Application Publication No. 2007/0249870. In the first step, the 8-arm PEG 10K chloride is made by reaction of thionyl chloride with the 8-arm PEG 10K octaalcohol. In the second step, the 8-arm PEG 10K chloride is reacted with aqueous ammonia to yield the 8-arm PEG 10K octaamine. A typical procedure is described here.

The 8-arm PEG 10K octaalcohol (M$_n$=10000; NOF SunBright HGEO-10000), (100 g in a 500-mL round-bottom flask) is dried either by heating with stirring at 85° C. under vacuum (0.06 mm of mercury (8.0 Pa)) for 4 hours or by azeotropic distillation with 50 g of toluene under reduced pressure (2 kPa) with a pot temperature of 60° C. The 8-arm PEG 10K octaalcohol is allowed to cool to room temperature and thionyl chloride (35 mL, 0.48 mol) is added to the flask, which is equipped with a reflux condenser, and the mixture is heated at 85° C. with stirring under a blanket of nitrogen for 24 hours. Excess thionyl chloride is removed by rotary evaporation (bath temp 40° C.). Two successive 50-mL portions of toluene are added and evaporated under reduced pressure (2 kPa, bath temperature 60° C.) to complete the removal of thionyl chloride. Proton NMR results from one synthesis are:

$^1$H NMR (500 MHz, DMSO-d6) δ 3.71-3.69 (m, 16H), 3.67-3.65 (m, 16H), 3.50 (s, ~800H).

The 8-arm PEG 10K octachloride (100 g) is dissolved in 640 mL of concentrated aqueous ammonia (28 wt %) and heated in a pressure vessel at 60° C. for 48 hours. The solution is sparged for 1-2 hours with dry nitrogen to drive off 50 to 70 g of ammonia. The solution is then passed through a column (500 mL bed volume) of strongly basic anion exchange resin (Purolite® A-860, The Purolite Co., Bala-Cynwyd, Pa.) in the hydroxide form. The eluant is collected and three 250-mL portions of de-ionized water are passed through the column and also collected. The aqueous solutions are combined, concentrated under reduced pressure (2 kPa, bath temperature 60° C.) to about 200 g, frozen in portions and lyophilized to give the 8-arm PEG 10K octaamine, referred to herein as P8-10-1, as a colorless waxy solid.

Preparation of 8-Arm PEG 10K Hexadecaamine (P8-10-2):

An 8-arm PEG 10K hexadecaamine, referred to herein as "P8-10-2", having two primary amine groups at the end of the arms, was prepared using a two step procedure, as described by Arthur in WO 2008/066787, in which 8-arm PEG 10K was reacted with methanesulfonyl chloride in dichloromethane in the presence of triethylamine to produce 8-arm PEG 10K mesylate, which was subsequently reacted with tris(2-aminoethyl)amine to give the 8-arm PEG 10K hexadecaamine. A typical synthesis is described here.

To a solution of 10 g of 8-arm PEG 10K ($M_n$=10,000; NOF, Tokyo, Japan) in 50 mL of dichloromethane stirred under nitrogen and cooled to 0° C. is added 2.2 mL of triethylamine, followed by 1.2 mL of methanesulfonyl chloride. The mixture is allowed to warm to room temperature and is stirred overnight. The reaction mixture is transferred to a separatory funnel and washed gently three times with 15 mL portions of 1 M potassium dihydrogen phosphate, followed by 15 mL of 1 M potassium carbonate, and then 15 mL of water. The dichloromethane layer is dried over magnesium sulfate, filtered, and concentrated by rotary evaporation to afford 11.17 g of 8-arm PEG 10K mesylate.

A mixture of 10 g of 8-arm PEG 10K mesylate and 45 mL of tris(2-aminoethyl)amine dissolved in 45 mL of water is stirred at room temperature for 24 hours. The reaction mixture is diluted with 45 mL of 5% (w/w) aqueous sodium bicarbonate and extracted with a total of 500 mL of dichloromethane divided in 3 portions. The dichloromethane solution is dried over sodium sulfate, and concentrated by rotary evaporation to 20 to 25 g. Ether (100 mL) is added to the concentrated dichloromethane solution with vigorous stirring, and the mixture is cooled to 0° C., causing a waxy solid to separate from solution. The solvent is decanted from the waxy solid, and the waxy solid is dried under vacuum to give the 8-arm PEG 10K hexadecaamine (P8-10-2).

Example 1

Preparation of Dextran Having Pendant Aldehyde Groups (AFD-15-90)

Dextran containing pendant aldehyde groups and having a weight-average molecular weight of about 15 kDa and a degree of aldehyde substitution of about 90% was prepared using a two step procedure. In the first step, dextran having a weight-average molecular weight of about 9 to about 11 kDa was reacted with allyl glycidyl ether to form an olefin intermediate, which was then reacted with ozone to form the dextran containing pendant aldehyde groups.

In the first step, 30 g of dextran (average molecular weight of 9-11 kDa, Sigma), and 30 mL of water were added into a 3-neck flask. The solution was cooled to 10° C. and then 39 mL of a 20 wt % NaOH solution was added. The resulting solution was stirred for 25 min, giving a faint yellow solution, and then 84.58 g (4 equiv) of allyl glycidyl ether (Aldrich) was added. The resulting mixture was heated to 65° C. for 5.5 hours, and then allowed to cool to room temperature, after which the pH was adjusted to 7.0 with 1 N HCl. The mixture was diluted with an additional 200 mL of water and purified using a Millipore Pellicon II ultrafiltration system (Millipore Corp., Billerica, Mass.), by filtration through 1 kDa cutoff filters with continuous replacement of filtrate with pure water until 5× the initial solution volume had been collected as filtrate. A small sample was taken and lyophilized for analytical purposes. The remainder of the filtrate was used directly in the subsequent ozonolysis step. The degree of substitution was determined to be 1.33 by proton NMR from the ratio of integration between the olefin peaks and the anomeric peaks at 4.8-5.0.

In the second step, 460 mL of the filtrate resulting from step 1 was added to a 3-neck, 2 L flask equipped with magnetic stir bar, and sparge tube inlet. The solution was cooled in an ice bath to 0-5° C. and then sparging with ozone was begun from an ozone generator (ClearWater Tech, LLC., San Luis Obispo, Calif.; Model CD10) at 100% power which generates 7% ozone. Foaming occurred, which was controlled by the addition of a few drops of 1-heptanol. Samples were taken at 6.25 and 7.75 hours and analyzed using 13-C NMR. Disappearance of resonances at 118 and 134 ppm indicated that the olefin had been consumed after 7.75 hours. Then, a solution of sodium sulfite (23.3 g in 138 mL water) was added dropwise with stirring. A slight exotherm was observed and the reaction mixture was allowed to stir overnight under nitrogen. The mixture was transferred to a 1 L glass jar and filtered through a Millipore Pellicon II ultrafiltration system with 1 kDa cutoff filters. Water was continuously added to replace the filtrate collected, and the retentate was recycled back to the glass jar. This process was continued until more than 5× the initial reaction volume had been collected in the filtrate. The purified solution was then frozen and lyophilized to give 53.9 g of a fluffy white solid. The degree of aldehyde substitution of the resulting solid product was determined to be 89% using the method of Zhao and Heindel (*Pharmaceutical Research* 8:400, 1991). The weight-average molecular weight of the aldehyde-functionalized dextran was determined to be about 15 kDa using size exclusion chromatography (SEC). This aldehyde-functionalized dextran is referred to herein as AFD-15-90.

A second preparation of this aldehyde-functionalized dextran was made using the same procedure. The degree of aldehyde substitution of the resulting product was determined to be 92% using the method of Zhao and Heindel and the weight-average molecular weight was found to be 16 kDa using SEC. This aldehyde-functionalized dextran is referred to herein as AFD-16-92.

Example 2

Preparation of Inulin Having Pendant Aldehyde Groups (AFI-12-49)

Inulin containing pendant aldehyde groups and having a weight-average molecular weight of about 12 kDa and a degree of aldehyde substitution of about 49% was prepared using the two step procedure described above.

In the first step, 20 g of inulin (average molecular weight of about 4 kDa, Sigma) was suspended in 200 mL of water, heated to 70° C. for 1 hour to dissolve, and then cooled to 65° C. To this solution was added 23 mL of sodium hydroxide solution (20 wt % in water), followed by the slow addition of allyl glycidyl ether (50.7 g) via a syringe pump at a rate of 3 mL/min. After the addition, the mixture was heated to 65° C. for 6 hours. After which time, the reaction mixture was cooled to room temp and neutralized to pH 7 with 50% HCl. The reaction mixture was purified by ultrafiltration over a 1000 MWCO membrane (collect 10× volume of waste).

$^1$H NMR (D$_2$O): d 5.95 ppm (m, integral 1.0, OCH$_2$C(H)=CH$_2$), 5.31 (dd, integral 2.1, OCH2(CH)=CH$_2$), 4.37 (br. s, integral 0.40), 4.25 (br. s, integral 0.76), 4.0-3.55 (br. m, integral 12.9).

In the second step, the filtrate was cooled to approximately 5° C. using an ice/water bath. Ozone was sparged into the stirred solution for 6 hours. 1-Heptanol was added (a few drops) to control foaming. At the end of the reaction, sodium sulfite solution (16 g in 100 mL water) was added to the cooled solution (cooled in an ice/water bath). The solution was stirred at room temperature overnight. The product was purified by ultrafiltration (MWCO 1000, collect 12× volume of waste). The filtrate was lyophilized to yield a white solid.

Size exclusion chromatography (SEC) analysis of the product gave the following: $M_w$=1.2×10$^4$, $M_n$=7.3×10$^3$, $M_z$=1.5×10$^4$, $M_w/M_n$=1.6.

The degree of aldehyde substitution was determined to be about 49% by titration of the hydroxylamine adduct of the inulin aldehyde using the method described by Zhao and Heindel (*Pharmaceutical Research* 8:400, 1991). This aldehyde-functionalized inulin is referred to herein as AFI-12-49.

Example 3

Preparation of Dextran Having Pendant Aldehyde Groups (AFD-7-86)

Dextran containing pendant aldehyde groups and having a weight-average molecular weight of about 5 to 11 kDa and a degree of aldehyde substitution of 86% was prepared using a two step procedure. In the first step, dextran having a weight-average molecular weight of about 5 to about 11 kDa was reacted with glycidol to form alkylated dextran. In the second step the alkylated dextran was oxidized with sodium periodate to oxidize the terminal diol groups added in the first step to give dextran having pendant aldehyde groups.

In the first step, 20 g of dextran (average molecular weight of 5-11 kDa, Sigma), was suspended in 20 mL of water and heated to 55° C. To this solution was added 25 mL of sodium hydroxide solution (20 wt % in water), followed by the slow addition of glycidol (36 g, Aldrich) using a syringe pump at a flow rate of 1.0 mL/min at 55° C. Then, the mixture was heated to 55° C. for 6 hours, after which the reaction mixture was cooled to room temperature. The product was washed twice with 20 mL of ether to remove excess reagent. The resulting yellow homogeneous mixture was neutralized with 50% HCl over ice (final pH was 7.3). The sample was precipitated in approximately 5× volume of cold isopropanol (~0° C.). The isopropanol layer was decanted off, the solid product washed with cold isopropanol, and the process of dissolution followed by precipitation was repeated two more times. The solid product was dried under vacuum for 48 hours.

In the second step, 15 g of the solid product from the first step was dissolved in 150 mL of water in a round bottom flask and then the resulting solution was cooled to 4° C. Sodium periodate solution (8.25 g in 85 mL of water) was added to the round bottom flask dropwise over 30 min. The reaction mixture was stirred at 4° C. for 2 hours, and then 10.4 g (9.3 mL) of ethylene glycol was added to the reaction mixture, which was then stirred for 10 min. The product was purified using a TFF System (Millipore Corp., Billerica, Mass.) with a 1000 molecular weight cut off membrane and freeze dried to yield 10 g of white powder. The degree of aldehyde substitution of the product was determined to be 86% by titration of the hydroxylamine adduct using the method described by Zhao and Heindel (*Pharmaceutical Research* 8:400, 1991).

Size exclusion chromatography (SEC) analysis of the product gave the following: $M_w$=7.4×10$^3$, $M_n$=4.8×10$^3$, $M_z$=1.1×10$^4$, $M_w/M_n$=1.5. This aldehyde-functionalized dextran is referred to herein as AFD-7-86.

Example 4

Preparation of Dextran Having Pendant Aldehyde Groups (AFD-9-120)

Dextran containing pendant aldehyde groups and having a weight-average molecular weight of about 9 kDa and a degree of aldehyde substitution of 120% was prepared using a two step procedure. In the first step, dextran having a weight-average molecular weight of about 5 to about 11 kDa was reacted with glycidol to form alkylated dextran. In the second step the alkylated dextran was oxidized with sodium periodate to oxidize the terminal diol groups added in the first step to give dextran having pendant aldehyde groups.

In the first step, three batches of dextran were reacted with glycidol to form the alkylated dextran. In two of the batches, 20 g of dextran (average molecular weight of 5-11 kDa, Sigma), was reacted with glycidol (36 g, Aldrich) in the same manner as described above, for the first step of the preparation of AFD-7-86. In the third batch, the mole ratio of glycidol to dextran was varied. Dextran (10 g) was dissolved in a solution formed by combining 10 mL of water and 12.5 mL sodium hydroxide solution (20 wt %). Glycidol (44 g, Aldrich) was added to the dextran solution using a syring pump at a rate of 0.7 mL/mn. The mixture was heated to 55° C. and 20 mL of water was added. The reaction mixture was heated at 55° C. for 6 hours. The product was isolated as described above for AFD-7-86. The three batches were combined to make a master batch of materials for the second step.

In the second step, 25 g of the solid product from the master batch described above was dissolved in 250 mL of water in a round bottom flask and then the resulting solution was cooled to 4° C. Sodium periodate solution (20.8 g in 125 mL of water) was added to the round bottom flask dropwise over 1 hour. The reaction mixture was stirred at 4° C. for 2 hours, and then 66 g of ethylene glycol was added to the reaction mixture, which was then stirred for 30 min. After which time, the reaction mixture was filtered. The filtrate was purified using a TFF System (Millipore Corp., Billerica, Mass.) with a 1000 molecular weight cut off membrane and freeze dried to yield 17 g of white powder. The degree of aldehyde substitution of the product was determined to be 120% by titration of the hydroxylamine adduct using the method described by Zhao and Heindel (*Pharmaceutical Research* 8:400, 1991).

Size exclusion chromatography (SEC) analysis of the product gave the following: $M_w$=8.9×10$^3$, $M_n$=6.8×10$^3$, $M_z$=1.2×10$^4$, $M_w/M_n$=1.3. This aldehyde-functionalized dextran is referred to herein as AFD-9-120.

Example 5

Preparation of Dextran Having Pendant Aldehyde Groups (AFD-13-64)

Dextran containing pendant aldehyde groups and having a weight-average molecular weight of about 13 kDa and a degree of aldehyde substitution of 64% was prepared using a two step procedure. In the first step, dextran having a weight-average molecular weight of about 5 to about 11 kDa was reacted with glycidol to form alkylated dextran. In the second step the alkylated dextran was oxidized with sodium periodate to oxidize the terminal diol groups added in the first step to give dextran having pendant aldehyde groups.

The first step was carried out as described above for AFD-9-120. In the second step, 25 g of the solid product from the master batch of the alkylated dextran described above for AFD-9-120 was dissolved in 250 mL of water in a round bottom flask and then the resulting solution was cooled to 4° C. Sodium periodate solution (10.4 g in 60 mL of water) was added to the round bottom flask dropwise over 1 hour. The reaction mixture was stirred at 4° C. for 2 hours, and then 6 g of ethylene glycol was added to the reaction mixture, which was then stirred for 30 min. Then the reaction mixture was filtered. The filtrate was purified using a TFF System (Millipore Corp., Billerica, Mass.) with a 1000 molecular weight cut off membrane and freeze dried to yield 17 g of white powder. The degree of aldehyde substitution of the product was determined to be 64% by titration of the hydroxylamine adduct using the method described by Zhao and Heindel (*Pharmaceutical Research* 8:400, 1991).

Size exclusion chromatography (SEC) analysis of the product gave the following: $M_w=1.3 \times 10^4$, $M_n=9.8 \times 10^3$, $M_z=1.8 \times 10^4$, $M_w/M_n=1.3$. This aldehyde-functionalized dextran is referred to herein as AFD-13-64.

Example 6

Preparation of Dextran Having Pendant Aldehyde Groups (AFD-13-46)

Dextran containing pendant aldehyde groups and having a weight-average molecular weight of about 13 kDa and a degree of aldehyde substitution of 46% was prepared using a two step procedure. In the first step, dextran having a weight-average molecular weight of about 9 to about 11 kDa was reacted with allyl glycidyl ether to form an olefin intermediate, which was then reacted with ozone to form the dextran containing pendant aldehyde groups.

In the first step, 30 g of dextran (average molecular weight of 9-11 kDa, Sigma), and 30 mL of water were added into a 3-neck flask. The solution was cooled to 10° C. and then 39 mL of a 20 wt % NaOH solution was added. The resulting solution was stirred for 25 min, giving a faint yellow solution, and then 42.27 g (2 equiv) of allyl glycidyl ether (Aldrich) was added. The resulting mixture was heated to 65° C. for 5.5 hours and then allowed to cool to room temperature, after which the pH was adjusted to 7.0 with 1 N HCl. The mixture was diluted with an additional 200 mL of water and purified with a Millipore Pellicon II ultrafiltration system (Millipore Corp., Billerica, Mass.) using 1 kDa cutoff filters with continuous replacement of filtrate with pure water until 5× the initial solution volume had been collected as filtrate. A small sample of the filtrate was taken and lyophilized for analytical purposes. The remainder of the filtrate was used directly in the subsequent ozonolysis step. The degree of substitution was found to be 0.84 by NMR, integrating the olefinic peaks relative to the anomeric resonances.

In the second step, 475 mL of the filtrate resulting from step 1 was added to a 3-neck, 2 L flask equipped with magnetic stir bar, and sparge tube inlet. The solution was cooled in an ice bath to 0-5° C. and then sparging with ozone was begun from an ozone generator (ClearWater Tech, LLC., San Luis Obispo, Calif.; Model CD10) at 100% power which generates 7% ozone. Foaming occurred, which was controlled by the addition of a few drops of 1-heptanol. Samples were taken at 2 and 4 hours and analyzed using 13-C NMR. Disappearance of resonances at 118 and 134 ppm indicated that the olefin had been consumed after 4 hours. Then, a solution of sodium sulfite (19.6 g in 117 mL of water) was added dropwise with stirring. A slight exotherm was observed and the reaction mixture was allowed to stir overnight under nitrogen. The mixture was transferred to a 1 L glass jar and filtered through a Millipore Pellicon II ultrafiltration system with 1 kDa cutoff filters. Water was continuously added to replace the filtrate collected, and the retentate was recycled back to the glass jar. This procedure was continued until more than 5× the initial reaction volume had been collected in the filtrate. The purified solution was then frozen and lyophilized to give 28.6 g of a fluffy white solid. The degree of aldehyde substitution of the resulting solid product was determined to be 46% using the method of Zhao and Heindel (*Pharmaceutical Research*, 1991, 8:400). The weight-average molecular weight of the aldehyde-functionalized dextran was determined to be about 13 kDa using size exclusion chromatography (SEC). This aldehyde-functionalized dextran is referred to herein as AFD-13-46.

Example 7

Preparation of Dextran Having Pendant Aldehyde Groups (AFD-19-64)

Dextran containing pendant aldehyde groups and having a weight-average molecular weight of about 19 kDa and a degree of aldehyde substitution of 60% was prepared using the two step procedure described above.

In the first step, 30 g of dextran (average molecular weight of 9-11 kDa, Sigma), and 30 mL of water were added into a 3-neck flask. The solution was cooled to 10° C. and then 39 mL of a 20 wt % NaOH solution was added. The resulting solution was stirred for 25 min, giving a faint yellow solution, and then 63.41 g (3 equiv) of allyl glycidyl ether (Aldrich) was added. The resulting mixture was heated to 65° C. for 5.5 hours, and then allowed to cool to room temperature, after which the pH was adjusted to 7.0 with 1 N HCl. The mixture was diluted with an additional 200 mL of water and purified using the Millipore Pellicon II ultrafiltration system, by filtration through 1 kDa cutoff filters with continuous replacement of filtrate with pure water until 5× the initial solution volume had been collected as filtrate. A small sample was taken and lyophilized for analytical purposes. The remainder of the filtrate was used directly in the subsequent ozonolysis step. The degree of substitution was determined to be 0.99 by NMR from the ratio of integration between the olefin peaks and the anomeric peaks at 4.8-5.0.

In the second step, 475 mL of the filtrate resulting from step 1 was added to a 3-neck, 2 L flask equipped with magnetic stir bar, and sparge tube inlet. The solution was cooled in an ice bath to 0-5° C. and then sparging with ozone was begun from an ozone generator (ClearWater Tech, LLC., San Luis Obispo, Calif.; Model CD10) at 100% power which generates 7% ozone. Foaming occurred, which was controlled by the addition of a few drops of 1-heptanol. Samples were taken at 4 and 5.75 hours and analyzed using 13-C NMR. Disappearance of resonances at 118 and 134 ppm indicated that the olefin had been consumed after 5.75 hours. Then, a solution of sodium sulfite (23.3 g in 139 mL water) was added dropwise with stirring. A slight exotherm was observed and the reaction mixture was allowed to stir overnight under nitrogen. The mixture was transferred to a 1 L glass jar and filtered through a Millipore Pellicon II ultrafiltration system with 1 kDa cutoff filters. Water was continuously added to replace the filtrate collected, and the retentate was recycled back to the glass jar. This process was continued until more than 5× the initial reaction volume had been collected in the filtrate. The purified solution was then frozen and lyophilized to give 39.1 g of a fluffy white solid. The degree of aldehyde substitution of the resulting solid product was determined to be 60% using the method of Zhao and Heindel (*Pharmaceutical Research*, 1991, 8:400). The weight-average molecular weight of the aldehyde-functionalized dextran was determined to be about 19 kDa using size exclusion chromatography (SEC). This aldehyde-functionalized dextran is referred to herein as AFD-19-64.

Examples 8-12

Stability of Aldehyde-Functionalized Dextrans in Aqueous Solution—Viscosity Measurements The purpose of these Examples was to demonstrate the higher stability of aldehyde-functionalized dextrans in aqueous solution compared to oxidized dextran D10-50 using viscosity measurements.

Aqueous solutions of oxidized dextran (25 wt %) and various aldehyde-functionalized dextrans (25 wt %), as shown in Table 1, were heated at 45° C. for 12 days. The viscosity of the aqueous solutions was measured at 30° C. at various time points. The results are summarized in Table 1.

TABLE 1

Viscosity of Aqueous Solutions of Oxidized dextran and Aldehyde-Functionalized Dextran

| Example | Dextran | Viscosity (cP) Day 0 | Viscosity (cP) Day 6 | Viscosity (cP) Day 12 | Viscosity Decrease after 12 days |
|---|---|---|---|---|---|
| 8 | AFD-13-64 | 17.37 | 17.35 | 17.94 | 0% |
| 9 | AFD-13-46 | 12.6 | 13.0 | 11.0 | 11% |
| 10 | AFD-19-64 | 15.7 | 17.6 | 15.1 | 4% |
| 11 | AFD-15-90 | 14.3 | 14.3 | 12.7 | 11% |
| 12, Comparative | D10-50 | 20 | 18 | 15.6 | 22% |

The results in Table 1 show that the aqueous solutions containing the aldehyde-functionalized dextrans having pendant aldehyde groups had a decrease in viscosity after 12 days ranging from 0% to 11%, whereas the viscosity of the aqueous solution containing the oxidized dextran decreased by 22% over the same time period. These results suggest that the aldehyde-functionalized dextrans having pendant aldehyde groups are more stable in aqueous solution than the oxidized dextran.

Examples 13-16

Stability of Aldehyde-Functionalized Dextrans in Aqueous Solution—Rheometry Measurements The purpose of these Examples was to demonstrate the stability of aldehyde-functionalized dextrans in aqueous solution. Oscillating disk rheometry of the hydrogels resulting from the reaction of the aldehyde-functionalized dextrans with multi-arm polyether amines was used as a measure of the stability of the aldehyde-functionalized dextran solutions.

Double barrel syringes containing an aqueous solution of various aldehyde-functionalized polysaccharides in one barrel and an aqueous solution of a multi-arm PEG amine in the other barrel, as shown in Table 2, were prepared in duplicate. Two other double barrel syringes were filed with an aqueous solution of oxidized dextran D10-50 in one barrel and an aqueous solution of P8-10-1 (20 wt %) in the other barrel. The aqueous solutions contained in the double barrel syringes were expressed through a static mixing tip onto the sample platform of a Model APA2000 rheometer (Alpha Technologies, Akron, Ohio), and the storage modulus (G') of the mixture was measured and taken as the value on Day zero. The value of G' at 60 seconds was taken as a measure of speed of gelation.

One group of the syringes was stored at 25° C. for various periods of time and the second group of syringes was heated at 40° C. for various periods of time (as shown in Table 2) to provide thermally aged aqueous solutions of the aldehyde-functionalized polysaccharides. The storage modulus of the mixed solutions was measured as described above at various times. The results are shown in Table 2, expressed as the percent of the Day zero G'.

TABLE 2

Rheometry Results of Hydrogel Formation

| Example | Alehyde-Functionalized Polysaccharide Solution | Multi-Arm PEG Amine Solution | Percent of Day 0 G' (60 sec) 25° C. | Percent of Day 0 G' (60 sec) 40° C. |
|---|---|---|---|---|
| 13 | AFD-15-90 (19 wt %) | P8-10-1 (20 wt %) | 94% (Day 20) | 56% (Day 20) |
| 14 | AFD-16-92 (20 wt %) | P8-10-1 (20 wt %) | 96% (Day 26) | 58% (Day 26) |
| 15 | AFI-12-49 (25 wt %) | P8-10-2/ P8-10-1 (2:1) 20 wt % | 94% (Day 26) | 81% (Day 26) |
| 16, Comparative | D10-50 (25 wt %) | P8-10-1 (20 wt %) | 75% (Day 30) | Did not gel (Day 30) |

The results in Table 2 suggest that the aldehyde-functionalized polysaccharides are more stable in aqueous solution than oxidized dextran.

Example 17

Thermal Stability of AFD-13-64 in Aqueous Solution Using Rheometry Measurements

The purpose of this Example was to demonstrate the thermal stability of aldehyde-functionalized dextran AFD-13-64 in aqueous solution using oscillating disk rheometry.

Two double barrel syringes, each containing an aqueous solution of AFD-13-64 (20 wt %) in one barrel and an aqueous solution of P8-10-1 (20 wt %) in the other barrel were prepared. One syringe was heated at 40° C. for 19 days; the other syringe was stored at 4° C. for the same period of time. Then, the storage modulus of the mixtures resulting from each syringe was measured using a Model APA2000 rheometer (Alpha Technologies, Akron, Ohio). The storage modulus obtained for the mixture resulting from the syringe that was stored at 40° C. for 19 days was essentially identical to that obtained from the mixture resulting from the syringe that was stored at 4° C. for the same period of time, suggesting that the aldehyde-functionalized dextran AFD-13-64 has good thermal stability.

Example 18, Comparative

Aldehyde-Functionalized Carboxymethyldextran Containing Pendant Aldehyde Groups Attached by an Amide Linkage The purpose of this Example was to demonstrate that an aldehyde-functionalized polysaccharide containing pendant aldehyde groups that are attached to the polysaccharide by an amide linkage is not as stable in aqueous solution as an aldehyde-functionalized polysaccharide containing pendant aldehyde groups that are attached to the polysaccharide by an ether linkage.

Preparation of 11 kDa Carboxymethyldextran with Degree of Carboxymethylation of 1.1 (CMDX-11-1.1):

Dextran having an average molecular weight of 8.5-11 kDa (Sigma) was dissolved in 123.75 mL of 6 N NaOH at 0° C. To this cold solution was added 30.75 g of chloroacetic acid (Aldrich). This reaction mixture was heated to 60° C. for 20 min, then cooled, and neutralized to pH 7.0 with concentrated HCl. The product was precipitated by adding the neutralized solution dropwise to 1.0 L of methanol. The solids were collected by filtration and re-precipitated from methanol. The entire procedure was then repeated three times to raise the degree of substituion to the desired level. After the final repeat, the product was further purified by ultrafiltration. The solution was diafiltered using a Millipore Pellicon II TFF system. A total of 6 volumes of permeate was collected while continuously adding water to maintain a constant retentate volume. The retentate was then collected and lyophilized to give 14.25 g of a fluffy white solid. The degree of carboxymethylation was determined by the method of Ho et al. (*Anal. Chem.* 52:916, 1980) to be 1.1. This carboxymethyldextran product is referred to herein as CMDX-11-1.1.

$^1$H NMR δ 4.9-5.2 mult. (1 H), 3.4-4.4 mult (9.5H).

Preparation of Aldehyde-Functionalized Carboxymethyldextran Containing Pendant Aldehyde Groups Attached by an Amide Linkage:

To a 3 liter, 3 necked flask was added 13.7 g of CMDX-60-1.7 and 916.6 mL of a 1:1 solution of teramethylethylene diamine buffer and dimethylformamide (DMF). A clear solution having a of pH 4.94 was formed. The pH was adjusted to 4.7 by addition of 1.0 M HCl. To the solution was added 47.74 g of 1-ethyle-3(3-dimethylaminopropyl)carbodiimide (Sigma) followed by 28.87 g of n-hydroxysuccinimide (Aldrich). The pH of the solution was readjusted to 4.7 and stirred for 2 hours. Then, 4-aminobutyraldehdye diethyl acetal (53.88 g) was added in portions over 3.5 hours so that the pH did not rise above 4.7. Toward the end of the reaction, the pH was allowed to rise to 6.25 and then the reaction mixture was stirred overnight. The reaction mixture was transferred to a glass jar, diluted with water and filtered on a Millipore Pellicon II ultrafiltration system with 1 kDa cutoff filters. A total of 5 volumes were collected as permeate while continuously recycling and adding fresh water to replace the permeate. The filtered solution was lyophilized to give a white solid product. The above procedure was then repeated starting with the white solid product to increase the loading of pendant acetal groups. The final yield was 20.3 g.

The acetal groups were removed by dissolving the solid in 400 mL of water and treating with 1.0 M HCl at pH 2.5 overnight. After neutralizing with NaOH, the solution was filtered on the Millipore Pellicon II ultrafiltration system as previously described and lyophilized to give 16.45 g of white solid. The molecular weight was determined by size exclusion chromatography to be 49 kDa. The degree of aldehyde substitution per ring was determined by NMR of the hydrolized sample to be 0.37. In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH).

Instability of the Aldehyde-Functionalized Carboxymethyldextran in Aqueous Solution:

An aqueous solution of aldehyde-functionalized carboxymethyldextran containing pendant aldehyde groups attached by an amide linkage was made by dissolving 5.1 g of the solid product obtained as described above in 15.3 g of autoclaved water. The mixture was shaken at 190 rpm in an incubator at 37° C. for 1 hour. The resulting solution was filtered through a 5.0 μm membrane and two 5 mL samples of the solution were placed in 55° C. incubator. After 19 hours both samples had formed amber gels which exhibited no flow.

Examples 19-33

In-Vitro Burst Testing of a Sealed Scalpel Incision in Swine Uterine Horn

The purpose of these Examples was to demonstrate the burst strength of a seal made with various hydrogels, which were formed using aldehyde-functionalized polysaccharides and multi-arm PEG amines, of an incision made in swine uterine horn.

A syringe pump system was used to measure the burst strength of a seal of an incision made in a section of swine uterine horn. The syringe pump (Model No. 22, Harvard Apparatus, Holliston, Mass.) was modified to be equipped with two 30 mL syringes, which were connected together through a "Y" junction. Water was pumped through a single piece of Tygon® R-36 tubing (0.6 cm diameter) and through a pressure gauge (Model PDG 5000L, Omega Engineering, Stamford, Conn.). An approximately 12.5 cm section of clean swine uterine horn, obtained from a local abattoir, was fitted on one end with a metal plug with a feed line fitting for water feed from the syringe pump and on the other end with a metal plug with a threaded hole which could be sealed with a machine screw. The plugs were held in place with nylon ties around the outside of the intestine. An incision was made through the uterine horn wall into the interior by puncturing with a Bard Parker™ surgical blade handle 5 (obtained from BD Surgical Products, Franklin Lakes, N.J.), fitted with a #15 surgical blade. The incision on the outside of the uterine horn was wider than the scalpel blade (typically 4-5 mm) while the hole through the inside wall was about 3 mm (about equal to the blade). This size incision mimics the distance between the interrupted sutures if an intestine were to be cut and later sutured. The uterine horn was filled with water containing a purple dye via the syringe pump until water began to leak from the open hole in the end plug and also from the scalpel puncture in the uterine horn wall. The pump was then turned off and the end plug was sealed with the machine screw. The scalpel incision site was blotted dry using a paper towel.

The aldehyde-functionalized polysaccharide and multi-arm PEG amine solutions, as shown in Table 3, were prepared in water with shaking overnight at 37° C. and 175 rpm. The two solutions were applied to the incision using a double barrel syringe (Mixpac Systems AG (Rotkreuz, Switzerland) fitted with a 16 or a 12 step static mixer (Mixpac Systems AG). After the application, the adhesive was allowed to cure at room temperature for no longer than 2 min. Burst pressure testing, also referred to herein as leak pressure testing, was done by pressurizing the sealed intestine with water from the syringe pump at a flow rate of 11 mL/min until the bioadhesive seal began to leak, at which point the pressure was recorded. Adhesive failure was attributed when the water leaked under the seal between the hydrogel and the tissue surface. Cohesive failure was attributed when the water penetrated and leaked through the hydrogel itself. The results of the burst testing are summarized in Table 3.

TABLE 3

Burst Pressure Testing Results

| Example | Aldehyde-Functionalized Polysaccharide Solution | Multi-Arm PEG Amine Solution | Ave Burst Pressure, psi |
|---|---|---|---|
| 19 | AFD-15-90 40 wt % | P8-10-1/P8-10-2 (1:2 w/w) 20 wt % | 1.2 (8.3 kPa) |
| 20 | AFD-15-90 40 wt % | P8-10-1/P8-10-2 (1:2 w/w) 30 wt % | 2.4 (16 kPa) |
| 21 | AFD-15-90 25 wt % | P8-10-1/P8-10-2 (1:2 w/w) 20 wt % | 2.8 (19 kPa) |
| 22 | AFD-15-90 25 wt % | P8-10-1/P8-10-2 (1:2 w/w) 10 wt % | 1.3 (9.0 kPa) |
| 23 | AFD-7-86 30 wt % | P8-10-1 50 wt % | 4.2 (29 kPa) |
| 24 | AFD-7-86 30 wt % | P8-10-2 20 wt % | 1.1 (7.6 kPa) |
| 25 | AFD-7-86 30 wt % | P8-10-1/P8-10-2 (9:1 w/w) 30 wt % | 2.7 (19 kPa) |
| 26 | AFD-9-120 25 wt % | P8-10-1 30 wt % | 3.0 (21 kPa) |
| 27 | AFD-9-120 25 wt % | P8-10-1/P8-10-2 (1:2 w/w) 25 wt % | 2.5 (18 kPa) |
| 28 | AFD-13-64 25 wt % | P8-10-1 30 wt % | 2.5 (18 kPa) |
| 29 | AFD-13-64 25 wt % | P8-10-1/P8-10-2 (1:2 w/w) 25 wt % | 4.2 (30 kPa) |
| 30 | AFI-12-49 40 wt % | P8-10-1/P8-10-2 (9:1 w/w) 30 wt % | 2.6 (18 kPa) |
| 31 | AFI-12-49 25 wt % | P8-10-1/P8-10-2 (9:1 w/w) 30 wt % | 2.8 (19 kPa) |
| 32 | AFI-12-49 40 wt % | P8-10-1/P8-10-2 (1:1 w/w) 30 wt % | 4.7 (32 kPa) |
| 33 | AFI-12-49 40 wt % | P8-10-1/P8-10-2 (1:2 w/w) 30 wt % | 4.2 (29 kPa) |

The results shown in Table 3 demonstrate that hydrogels formed by reacting an aldehyde-functionalized polysaccharide containing pendant single aldehyde groups with a mixture of an eight-arm branched end polyethylene glycol amine having two primary amine groups at the end of the polymer arms (i.e. P8-10-2) and an eight-arm polyethylene glycol amine (P8-10-1) having one primary amine group at the end of the polymer arms, adhered well to and sealed biological tissue.

Examples 34-43

In Vitro Biocompatibility Testing—Cytotoxicity

The purpose of these Examples was to demonstrate the safety of hydrogels resulting from the reaction of an aldehyde-functionalized polysaccharide with a multi-arm PEG amine in an in vitro test.

The testing was done using NIH3T3 mouse fibroblast cell cultures according to ISO10993-5:1999. The NIH3T3 mouse fibroblast cells were obtained from the American Type Culture Collection (ATCC; Manassas, Va.) and were grown in Dulbecco's modified essential medium (DMEM), supplemented with 10% fetal calf serum.

NIH3T3 mouse fibroblast cell cultures were challenged with hydrogels made by combining equal volumes of an aqueous solution of an aldehyde-funtionalized polysaccharide and an aqueous solution of multi-arm PEG amine, as shown in Table 4. The aqueous solutions were prepared and mixed to form hydrogels as described in Examples 19-33. Each hydrogel was placed in the bottom of a well in a polystyrene culture plate such that about ¼ of the well bottoms were covered. The wells were then sterilized under UV light and seeded with 50,000-100,000 NIH3T3 cells.

The cells grew normally confluent and coated the well bottom, growing up to the edges of the hydrogels; however, they did not overgrow the hydrogels. These results, summarized in Table 4, demonstrate a lack of cytotoxicity of the hydrogels, as well as the lack of adhesion of cell cultures to the hydrogels.

TABLE 4

Cytotoxicity Results

| Example | Aldehyde-Functionalized Polysaccharide Solution | Multi-Arm PEG amine solution | Cytotoxicity |
|---|---|---|---|
| 34 | AFI-12-49 25 wt % | P8-10-1/P8-10-2 (9:1 w/w) 30 wt % | nontoxic |
| 35 | AFI-12-49 40 wt % | P8-10-1/P8-10-2 (1:1 w/w) 30 wt % | nontoxic |
| 36 | AFI-12-49 40 wt % | P8-10-1/P8-10-2 (1:2 w/w) 25 wt % | nontoxic |
| 37 | AFD-9-120 25 wt % | P8-10-1 30 wt % | nontoxic |
| 38 | AFD-9-120 25 wt % | P8-10-1/P8-10-2 (1:2 w/w) 25 wt % | nontoxic |
| 39 | AFD-13-64 25 wt % | P8-10-1 30 wt % | nontoxic |
| 40 | AFD-13-64 25 wt % | P8-10-1/P8-10-2 (1:2 w/w) 25 wt % | nontoxic |
| 41 | AFD-15-90 25 wt % | P8-10-1/P8-10-2 (1:2 w/w) 20 wt % | nontoxic |
| 42 | AFD-15-90 40 wt % | P8-10-1/P8-10-2 (1:2 w/w) 20 wt % | nontoxic |
| 43 | AFD-15-90 40 wt % | P8-10-1/P8-10-2 (1:2 w/w) 30 wt % | nontoxic |

Example 44

Preparation of Dextran Having Pendant Dialdehyde Groups (DAFD-10-16)

Dialdehyde-functionalized dextran in which the pendant dialdehyde groups are linked to the dextran backbone by an ether bond was prepared using a three step procedure.

Step 1:

To a 300 mL, two-neck flask equipped with a magnetic stir bar and nitrogen inlet was added 74.3 mL of a 40 wt % sodium hydroxide solution and 0.94 g (2.91 mmol) of tetrabutylammonium bromide. The solution was cooled to 5-10° C. and treated with 5.0 g (59.44 mmol) of 3-cyclopentene-1-ol followed by dropwise addition of epichlorohydrin 22.0 g (237.76 mmol) over a 20 min period. The reaction mixture was stirred at room temperature overnight. Then, the reaction mixture was poured onto approximately 50 mL of ice/water and stirred to give a solution, which was extracted three times with 50 mL portions of diethyl ether. The combined organic layers were washed with brine solution until neutral to litmus and dried over $MgSO_4$. The solvent was removed on a rotary evaporator to yield a brown liquid. The crude product was purified by distillation. The product was collected at 118° C. and 25 mm Hg (3.3 kPa).

$^1$H NMR in $CDCl_3$ δ ppm (2.42,m, 2H; 2.5,m 1H; 2.6,m, 2H, 2.78,m, 1H; 3.15,m, 1H;3.4,m, 1H; 3.65-3.68,m, 1H;4.26,m, 1H; 5.68s,2H)

Step 2:

Into a 10 mL, 2-neck flask equipped with a magnetic stir bar and reflux condenser with nitrogen inlet was placed 0.58 mL of water followed by 0.5778 g (3.567 mmol) of dextran having a weight-average molecular weight of about 9 to about 11 kDa. The solution was stirred to form a suspension. To the flask was added 0.75 mL of 20 wt % NaOH solution. After stirring for 30 min, 1.0 g (7.134 mmol) of glycidyl 3-cyclopentenyl ether was added. The solution was heated in an oil bath at 65° C. for 5.5 hours. Then, the reaction mixture was cooled to room temperature and the pH was adjusted to 7.0 with 0.5 M HCl. The resulting solution was diluted to approximately 400 mL with water, then purified using the Millipore Pellicon II ultrafiltration system with a 1000 molecular weight cutoff cassette. A small aliquot was lyophilized for analysis.

$^1$H NMR was obtained in $D_2O$. δ ppm (2.2,d; 2.4,d; 3.31-3.7,m;4.1,s;4.77,s;4.9,s(b); 5.55, s)

The remainder of the solution was treated with ozone to make functionalized dextran. From NMR, the degree of substitution was determined by integration of the anomeric peaks at 5.0-5.2 ppm vs. the olefinic peaks. The degree of substitution was found to be 0.52.

Step 3:

A 1 L, 3-neck flask containing 400 mL of the aqueous solution of functionalized dextran (from the previous step) at approximately 8° C. was sparged with ozone for 5.5 hours. The ozone flow was stopped and a solution of 0.45 g of sodium sulfite in 3 mL of water was added to the flask at 8° C. The solution was stirred overnight and purified by ultrafiltration on the Millipore Pellicon II ultrafiltration system using 1000 MWCO cassette. The final solution was frozen and lyophilized to yield 0.68 g of a foam-like solid.

$^1$H NMR was obtained in $D_2O$. δ ppm (1.318,m; 1.523,m; 1.8,m; 2.1,m; 2.3-2.48,m; 3.3-3.9,m; 4.9,s; 5.1, s(b); 5.5,s)

The degree of aldehyde substitution was determined to be about 16% by titration of the hydroxylamine adduct of the dialdehyde-functionalized dextran using the method described by Zhao and Heindel (*Pharmaceutical Research* 8:400, 1991). This dialdehyde-functionalized dextran is referred to herein as DAFD-10-16.

Examples 45 and 46

In Vitro Degradation of Hydrogels Formed Using Dialdehyde-Functionalized Dextrans These Examples demonstrate the higher stability of a hydrogel prepared using aldehyde-functionalized dextran having pendant dialdehyde groups where the linkage to the dextran backbone is an ether linkage (Example 45) compared to a hydrogel prepared using aldehyde-functionalized dextran having pendant dialdehyde groups where the linkage to the dextran backbone is an ester linkage (Example 46, Comparative)

Preparation of Dextran Having Pendant Dialdehyde Groups (DAFD-Ester Linked):

Dialdehyde-functionalized dextran in which the pendant dialdehyde groups are linked to the dextran backbone by an ester bond was prepared using a two step procedure.

Step 1:

Into a 50 mL, 3-neck flask equipped with magnetic stir bar and a reflux condenser was placed 22 mL of dimethylacetamide (DMAC) followed by 1.817 g (11.217 mmol) of dextran having a weight-average molecular weight of about 9 to about 11 kDa and 1.09 g (25.71 mmol) of lithium chloride. A suspension formed, which was heated to 90° C. for one hour until a clear solution resulted. The solution was cooled to room temperature and 0.91 mL (11.217 mmol) of pyridine was added followed by dropwise addition of 2.18 g (11.217 mmol) of 3-cyclopentene carbonyl chloride. 4-Dimethylaminopyridine (DMAP, Aldrich) (30 mg) was added and the mixture was heated mixture at 60° C. overnight i.e., approximately 20 hours). After cooling, the resulting brown solution was added dropwise to 200 mL of cooled water with stirring to give a yellow solution. The pH was adjusted from 2.15 to 6.0 using 0.25 N NaOH solution. The crude product was purified on a Millipore Pellicon II ultrafiltration system using a 1000 molecular weight cutoff cassette. A small aliquot was frozen and lyophilized to obtain an analytical sample.

$^1$H NMR. δ ppm (2.59-2.66,m); (2.85,s); (3.0,s); (3.24(b), s); (3.46-3.51,m); (3.52-3.71,m); (3.84,d); (3.93,d); (4.91, s); (4.97,s); (5.12,t); (5.68,s)

Step 2:

A 1 L, 3-neck flask equipped with a magnetic stir bar and containing 350 mL of the solution resulting from the previous step at approximately 8° C. was sparged with an ozone stream for 5 hours. After discontinuing the ozone sparge, a solution of 1.41 g of sodium sulfite in 8.4 mL water was added. The resulting mixture was stirred at room temperature overnight, then purified on a Millipore Pellicon II ultrafiltration system using a 1000 molecular weight cutoff cassette filter. The solution was frozen and lyophilized to yield 1.92 g of a white solid.

$^1$H NMR was submitted in $D_2O$. δ ppm (3.49-3.79,m); (3.89-3.97,m); (4.97 d, (broad)); 5.16(s, (b))

This dialdehyde-functionalized dextran is referred to herein as DAFD-Ester Linked.

Preparation and Stability of Hydrogels

An aqueous solution containing dialdehyde-functionalized dextran DAFD-10-16 (Example 45) or DAFD-10-Ester Linked (Example 46, Comparative) at a concentration of 20 wt % was mixed with an aqueous solution contianing multi-arm PEG amine P8-10-1 (25 wt %) to form a hydrogel, as described in Examples 19-33. After the hydrogels cured, the samples were weighed and placed inside jars containing PBS (phosphate buffered saline) at pH 7.4. The jars were placed inside a temperature-controlled shaker set at 80 rpm and 37° C. The samples were removed from the jars at various times, blotted to remove excess solution, and weighed. Then, the samples were returned to the jars. The results are summarized in Table 5. The percent swell reported in the table is the weight of the hydrogel measured during the course of the study divided by the initial weight of the hydrogel, multiplied by 100.

TABLE 5

In Vitro Degradation of Hydrogels

| Example | Aldehyde-Functionalized Polysaccharide Solution | Multi-Arm PEG Amine Solution | Time (hours) | % Swell |
|---|---|---|---|---|
| 45 | DAFD-10-16 20 wt % | P8-10-1 25 wt % | 0 | 100 |
| | | | 1 | 249 |
| | | | 2 | 258 |
| | | | 4 | 245 |
| | | | 6 | 244 |
| | | | 8 | 243 |
| | | | 22 | 244 |
| | | | 26 | 247 |
| 46 Comparative | DAFD-Ester Linked 20 wt % | P8-10-1 25 wt % | 0 | 100 |
| | | | 1 | 236 |
| | | | 2 | 45.3 |
| | | | 4 | 3.6 |

These results demonstrate that hydrogels formed using aldehyde-functionalized dextran having pendant dialdehyde groups where the linkage to the dextran backbone is an ether linkage and the multi-arm PEG amine P-8-10-1 (Example 45) are much longer lived than hydrogels formed using aldehyde-functionalized dextran having pendant dialdehyde groups where the linkage to the dextran backbone is an ester linkage and the multi-arm PEG amine P-8-10-1 (Example 46, Comparative).

What is claimed is:

1. A composition comprising at least one aldehyde-functionalized polysaccharide containing pendant aldehyde groups, said aldehyde-functionalized polysaccharide having a weight-average molecular weight of about 3,000 to about 250,000 Daltons and a degree of aldehyde substitution of greater than 40% to about 200%; wherein:
   (i) said pendant aldehyde groups are attached to the polysaccharide through linking groups which do not contain a nitrogen atom;
   (ii) said linking groups are attached to the polysaccharide by ether linkages; and
   (iii) said linking groups contain an alkoxy group alpha to the pendant aldehyde group.

2. The composition according to claim 1 wherein the degree of aldehyde substitution is 40% to about 120%.

3. The composition according to claim 1 wherein the aldehyde-functionalized polysaccharide is selected from the group consisting of aldehyde-functionalized derivatives of: dextran, carboxymethyldextran, starch, agar, cellulose, hydroxyethylcellulose, carboxymethylcellulose, pullulan, inulin, levan, and hyaluronic acid.

4. The composition according to claim 3 wherein the aldehyde-functionalized polysaccharide is aldehyde-functionalized dextran.

5. The composition according to claim 3 wherein the aldehyde-functionalized polysaccharide is aldehyde-functionalized inulin.

6. The composition according to claim 1 wherein the weight-average molecular weight is about 7,000 to about 20,000 Daltons.

7. The composition according to claim 1 wherein the composition is in the form of an aqueous solution or dispersion.

8. The composition according to claim 7 wherein the aqueous solution or dispersion contains the aldehyde-functionalized polysaccharide at a concentration of about 5% to about 40% by weight relative to the total weight of the solution or dispersion.

* * * * *